(12) United States Patent
Boock (10) Patent No.: US 6,309,367 B1
(45) Date of Patent: Oct. 30, 2001

(54) ANEURYSM SHIELD

(75) Inventor: Robert Boock, Minnetonka, MN (US)

(73) Assignee: NeuroVasx, Inc., Maple Grove, MN (US)

(*) Notice: Subject to any disclaimer, the term of this patent is extended or adjusted under 35 U.S.C. 154(b) by 0 days.

(21) Appl. No.: 09/360,026

(22) Filed: Jul. 23, 1999

(51) Int. Cl.[7] .................................................. A61F 5/00
(52) U.S. Cl. ............................. 602/1; 623/1; 623/12; 606/191; 606/198
(58) Field of Search ..................... 602/1; 623/1, 11–12; 600/36; 606/191, 194–195, 198

(56) References Cited

U.S. PATENT DOCUMENTS

| 5,154,179 | 10/1992 | Ratner | 128/653.4 |
|---|---|---|---|
| 5,354,295 | 10/1994 | Guglielmi et al. | 606/32 |
| 5,405,379 | 4/1995 | Lane | 623/1 |
| 5,720,776 | * 2/1998 | Chuter et al. | |
| 5,769,882 | * 6/1998 | Fogarty et al. | |
| 5,817,017 | 10/1998 | Young et al. | 600/433 |
| 5,843,158 | * 12/1998 | Lenker et al. | |
| 5,925,074 | * 7/1999 | Gingras et al. | |

* cited by examiner

Primary Examiner—Michael A. Brown
Assistant Examiner—Lalita M. Hamilton (57) ABSTRACT

The present invention includes a device for covering an aneurysm. The device includes an elastic main body that has a symmetry effective for covering an aneurysm and one or more anchor rings for anchoring the main body about the aneurysm.

18 Claims, 10 Drawing Sheets

ANEURYSM SHIELD

BACKGROUND OF THE INVENTION

The present invention relates to an aneurysm seal and to a method for sealing an aneurysm.

Cerebral aneurysms are formed by an out-pouching of normal cerebral vasculature at a number of sites. The sites tend to be areas of mechanical stress concentration. Fluid flow appears to be a likely initiating cause for the formation of these aneurysms. The nature of an underlying difference in vascular wall structure in people who develop an aneurysm at a stress concentration site, also infers a genetic root cause for this disease.

Treatment options presently available for cerebral aneurysms include surgical treatment and interventional treatment. Surgical treatment has been a longheld standard of care for the treatment of aneurysms. Surgical treatment involves a long and delicate operative procedure that has significant risks and a long period of post-operative rehabilitation and critical care.

Interventional treatment has included a use of neuro-interventional devices such as the Gugliema detachable coils (GDC). The use of these types of interventional devices has not entirely replaced surgery because of a number of technical details, as well as a belief among physicians that this type of treatment is not curative for the long term. The treatment is not believed to be curative because a placement of platinum coils within an aneurysm provides protection from fluid stress concentration, but does not allow for healing of the aneurysmal opening. Surgical procedures do allow for endolithial cell closure of the aneurysm and thus, ultimately, a cure for the disease.

There is then a need for a minimally invasive interventional device for the treatment of aneurysm that encourages or provides a closure or growth across the neck of the aneurysm.

SUMMARY OF THE INVENTION

One embodiment of the present invention includes a device for covering an aneurysm. The device includes an elastic main body that has a symmetry effective for covering an aneurysm. The device also includes one or more anchor rings for anchoring the main body about an aneurysm.

Another embodiment of the present invention includes a method for treating an aneurysm. The method includes providing an elastic main body that has a symmetry effective for covering the aneurysm and one or more anchor rings for anchoring the main body about the aneurysm. The main body is positioned about the aneurysm. Anchor rings are deployed at one or more locations of the main body.

One other embodiment includes a method for repairing an aneurysm. The method includes providing an elastic main body that is positionable over an aneurysm. Cell growth factors, genes, gene products, and so on, are imparted to the main body to promote cell growth over the aneurysm. The main body is anchored over the aneurysm with an anchoring mechanism.

Another embodiment of the present invention includes a device for treating an aneurysm. The device comprises an elastic main body that has a symmetry effective for covering an aneurysm. The device also includes an anchoring mechanism for anchoring the main body over the aneurysm. The device additionally includes a swellable material attached to the main body wherein the swellable material is effective for substantially filling the neck of the aneurysm.

DETAILED DESCRIPTION

Figure 1:
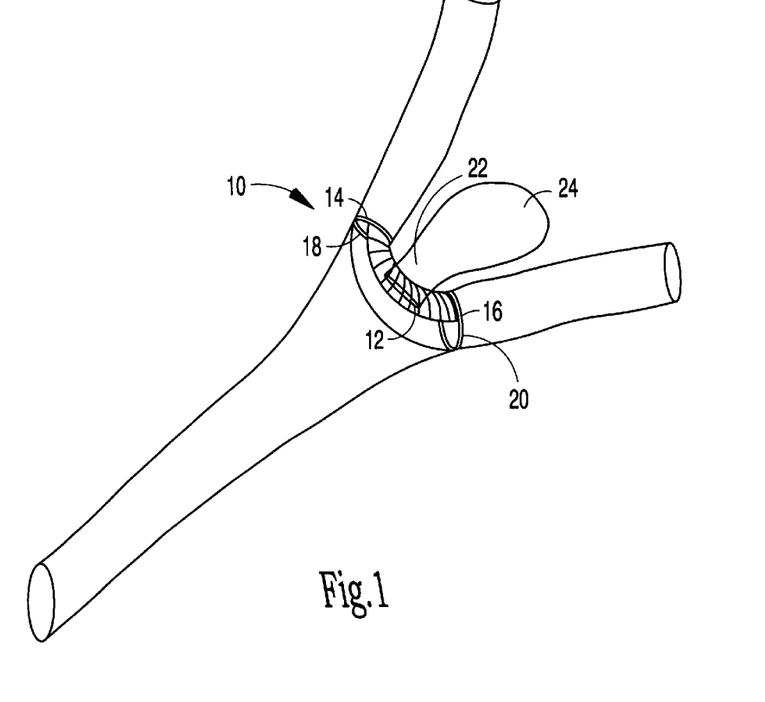
FIG. 1 is a perspective view of one embodiment of an aneurysm shield of the present invention positioned at a terminal bifurcation in situ.

The aneurysm shield of the present invention illustrated at a terminal bifurcation site in situ at 10 in FIG. 1 includes an elastic, polymeric main body 12 and anchor rings 14 and 16 positioned at ends 18 and 20 of the main body 12 in order to anchor the aneurysm shield over a neck 22 of an aneurysm 24. The anchor rings 14 and 16 are substantially rigid when in a securing conformation, such as is shown in FIGS. 1 and 2.

Figure 2:
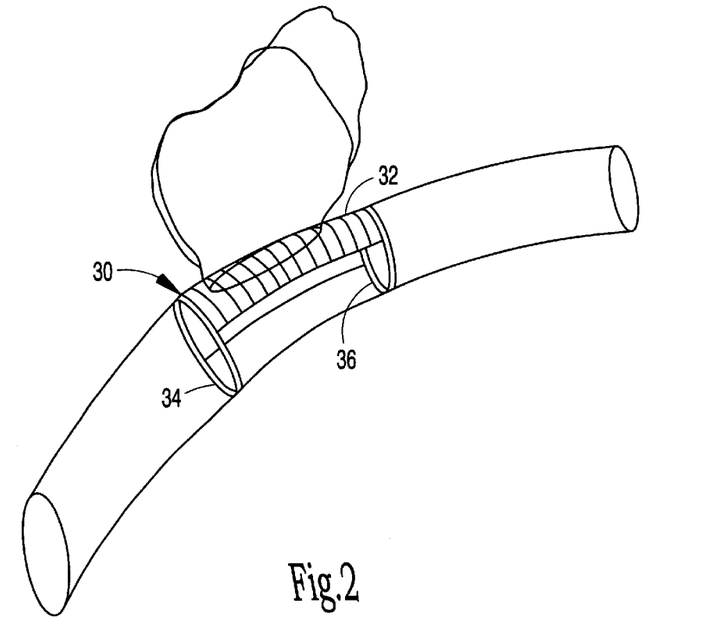
FIG. 2 is a perspective view of one other embodiment of an aneurysm shield of the present invention positioned at a vessel sidewall in situ.
Figure 3:
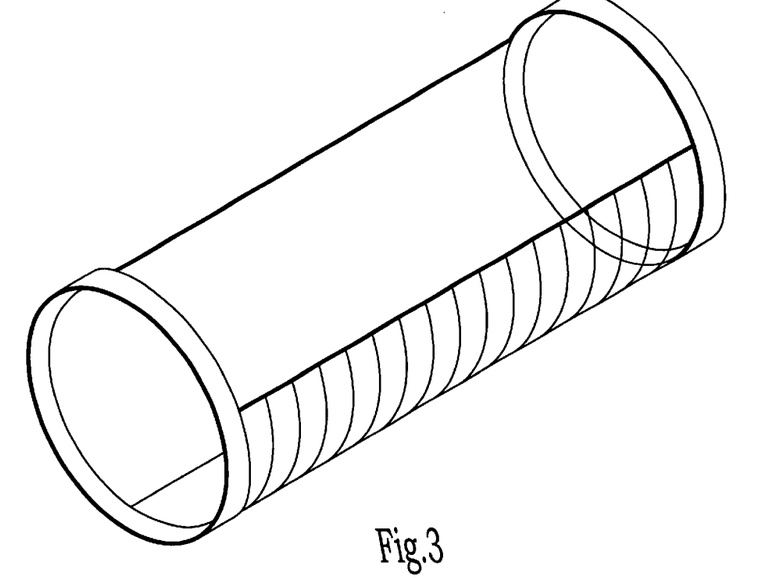
FIG. 3 is a perspective view of one embodiment of the aneurysm shield of the present invention for use with an aneurysm.
Figure 4:
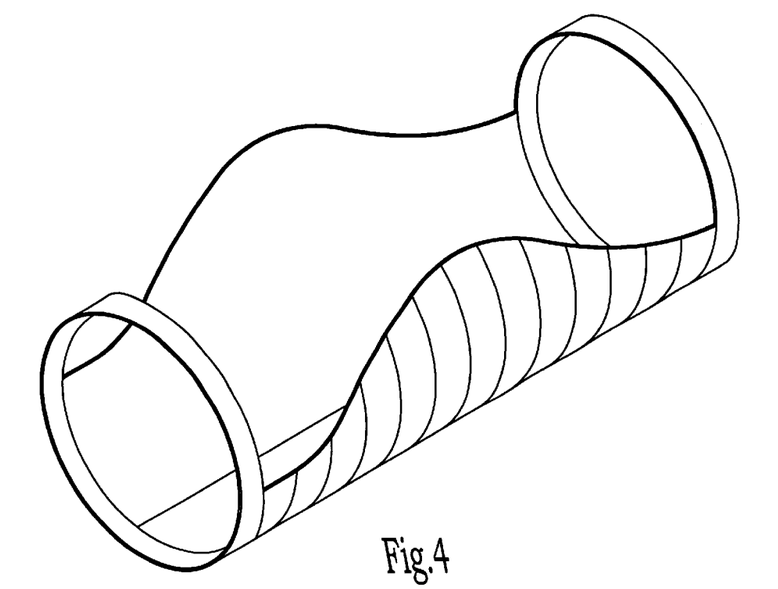
FIG. 4 is a perspective view of another embodiment of an aneurysm shield of the present invention for use with an aneurysm.
Figure 5:
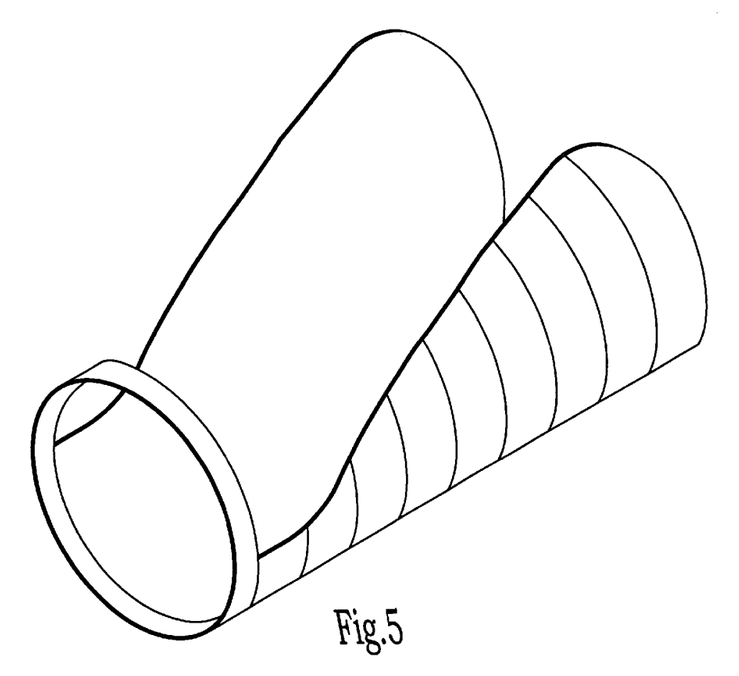
FIG. 5 is a perspective view of one other embodiment of an aneurysm shield of the present invention with no distal anchor.
Figure 6:
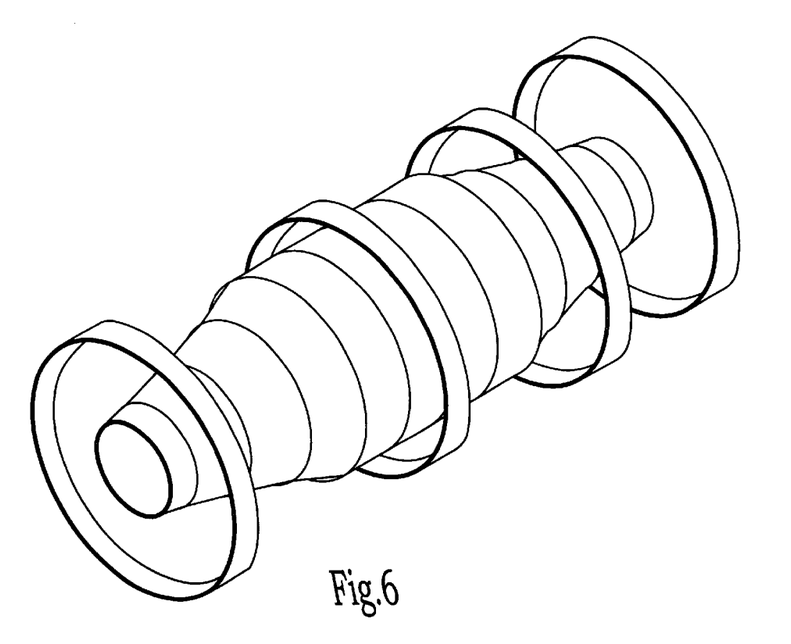
FIG. 6 is a perspective view of a multiple ring aneurysm shield embodiment of the present invention.
Figure 7:
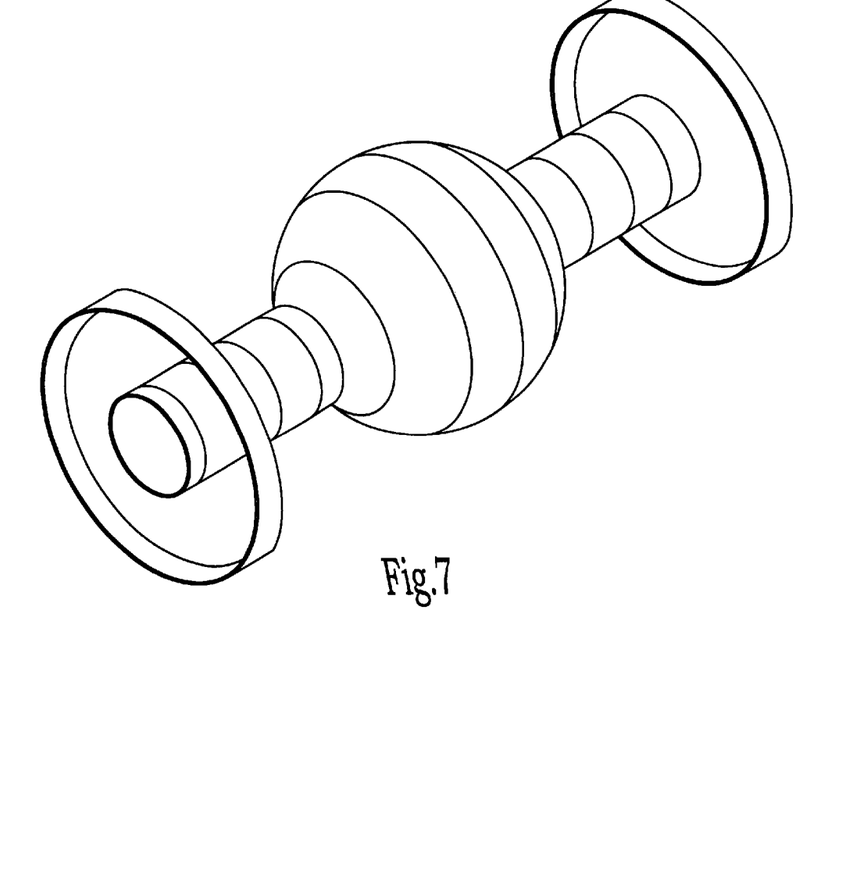
FIG. 7 is a perspective view of another aneurysm shield embodiment of the present invention.
Figure 8:
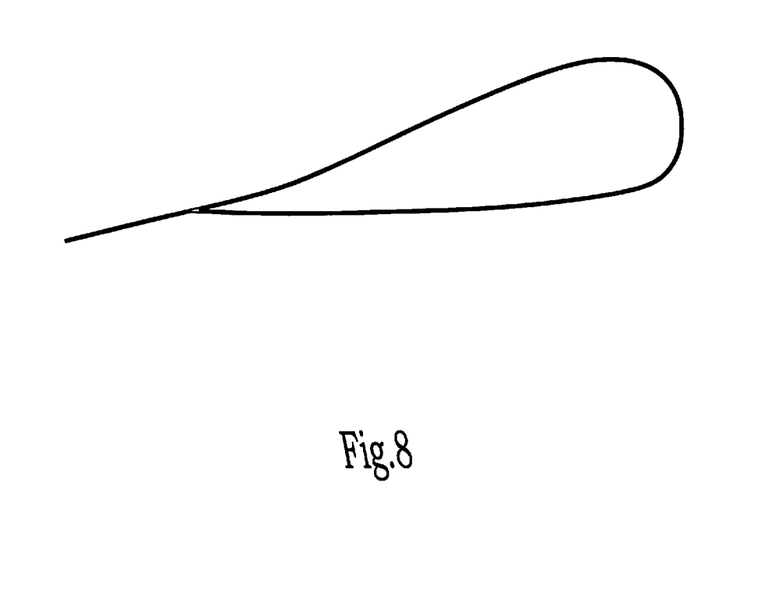
FIG. 8 is a leading profile view of an anchor ring of the present invention.

The aneurysm shield of the present invention may be fabricated to fit over an aneurysm located at a terminal bifurcation such as is shown at 10 in FIG. 1, or a sidewall, such as is shown for aneurysm shield 30 in FIG. 2. Aneurysm shield 30 also includes a main body 32 with anchor rings 34 and 36. The aneurysm shields 10 and 30 have a generally half-cylindrical shape that is anchored to a vessel wall in order to cover an aneurysm. Other aneurysm shields such as are shown in FIGS. 6 and 7 are also usable in the method of the present invention to accommodate other local vessel anatomies.

The main body of the aneurysm shield, such as 12 or 32 is typically an elastic polymeric membrane material such as hydrogel, chitosan, alginate, siloxane, and so forth. The membrane material is a biocompatable material. One cross-sectional view of the aneurysm shield of the present invention is shown at 50 in FIG. 12. The cross-sectional view shows a core 52 that is comprised of the hydrogel, chitosan, alginate, and so forth. Surrounding the core 52 and facing the blood flow is a layer 54. This layer 54 is impregnated or coated with materials that promote cell growth, such as fibronectin, collagen, basement membrane proteins, integrins, and so forth. It is desired that endothelial cells adhere to the main body and grow to encapsulate the inner surface of the shield and seal the aneurysm opening.

Figure 12:
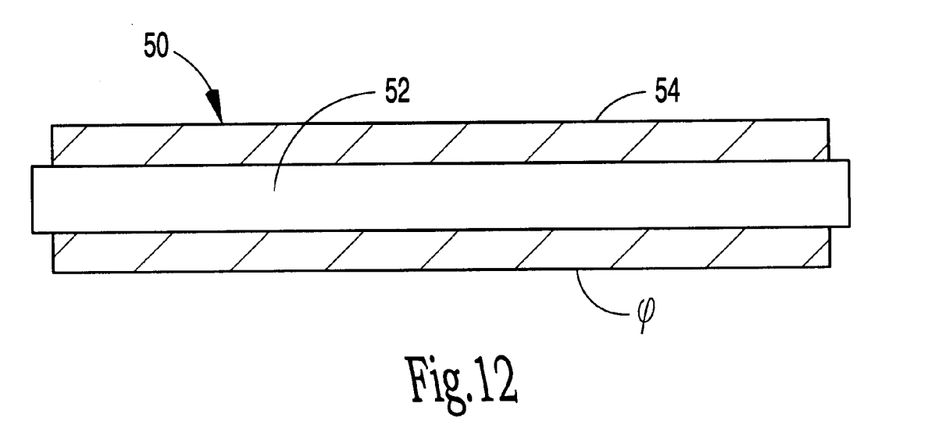
FIG. 12 is a cross-sectional view of an aneurysm shield of the present invention.

Opposing this layer is a layer 56 that faces the blood vessel wall. This layer 56 is impregnated or coated with materials that have a negative charge and or have a coating of proteins and integrins. The layer 56 is sticky and/or charged in order to facilitate attachment and holding of the aneurysm shield. The total thickness of the aneurysm shield main body is maximally about 0.5 millimeters.

The aneurysm shield of the present invention is typically fashioned, for some embodiments, into a generally half-cylindrical aneurysmal opening covering which is anchored to a vessel wall. The material of the shield and conformation of the shield predispose the shield to adhere to the vessel wall because of the nature of coating on an exterior surface, such as 56. The coating comprises a number of activated attachment chemistries, such as charge attraction, negatively charged surfaces, as use of integrins to attach to the cell surface structure, or polymerization on the surface such as glueing.

The exterior surface 54 facing the blood flow is coated with collagen, fibronectin, basement membrane proteins, and so on. The base membrane material is made so that endolithial cells readily grow and adhere to effectively encapsulate the material and seal the aneurysm opening.

Aneurysm shield embodiments such as are shown in FIGS. 3, 4, 5 6 and 7 are utilized to shield or cover aneurysms associated with particular types of vessel symmetry. The shield embodiment shown in FIG. 5 requires only one anchor ring.

Figure 9A:
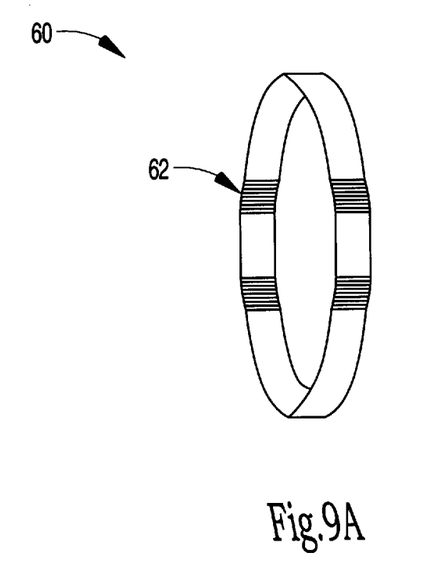
FIG. 9A is a perspective view of an anchor ring of the present invention in a closed position.
Figure 9B:
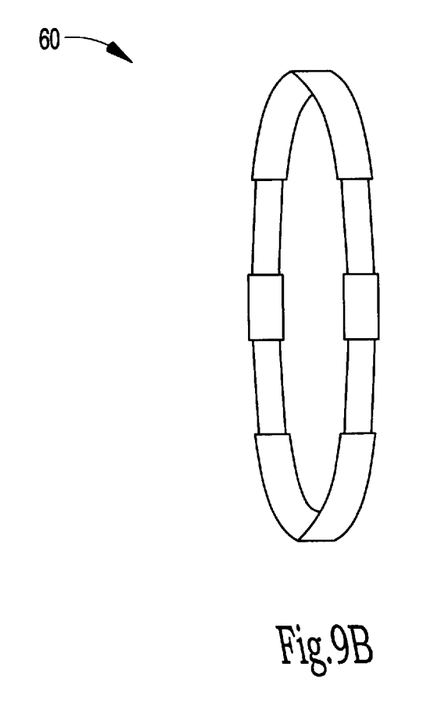
FIG. 9B is a perspective view of the anchor ring of FIG. 9A in an open position.
Figure 10:
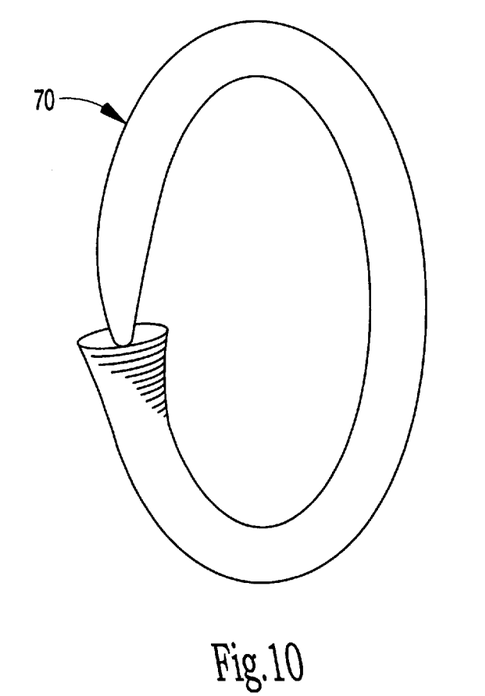
FIG. 10 is a perspective view of a separate embodiment of an anchor ring of the present invention in an open position.
Figure 11:
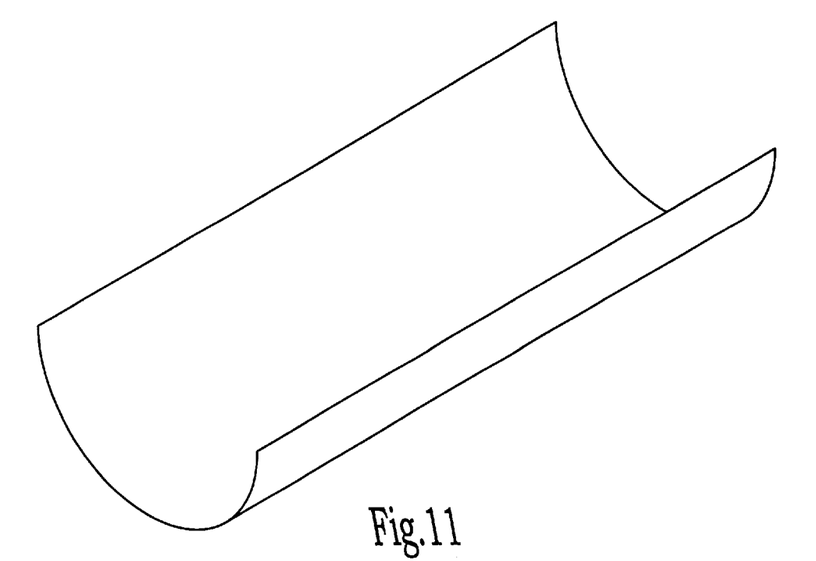
FIG. 11 is a perspective view of one embodiment of an aneurysm shield of the present invention.

Anchor rings are comprised of stent-like rings. The anchor rings may be either self-expanding or balloon expandable. The unexpanded rings have a thickness that is about the thickness of a catheter marker band. For instance, rings such as are shown at 60 or 70 in FIGS. 9A, 9B and 10 are self expandable rings. These rings self-expand when unconstrained. FIG. 9A shows anchor ring 60 in a closed position. FIG. 9B shows anchor ring 60 in an open position. These anchor rings comprise an expandable segment 62 that expands when positioned in an open area. Self-expanding anchor ring 60 may comprise more than one expandable region. The small longitudinal size of these anchor rings allows for easy traversing of the tortuosity of the cerebral anatomy but provides for sufficient anchoring of the sticky polymeric material to prevent any potential migration of the material.

Figure 16:
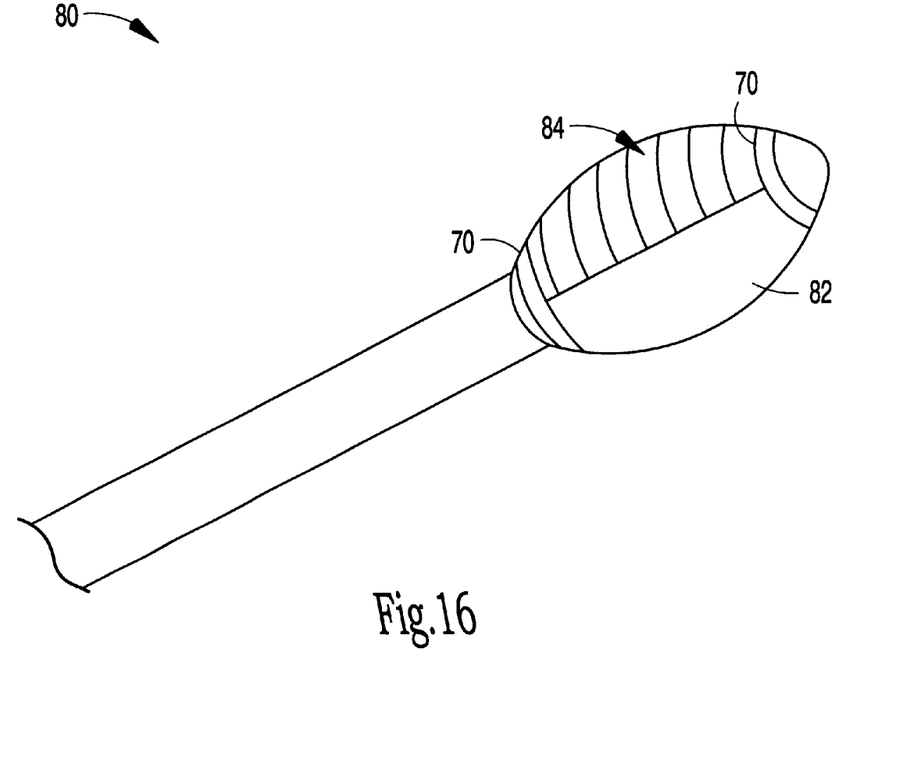
FIG. 16 is one embodiment of an aneurysm shield of the present invention expanded by a balloon.
Figure 17:
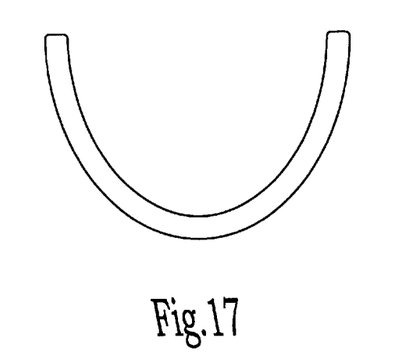
FIG. 17 is one embodiment of a membrane component of the aneurysm shield of the present invention in an open position.
Figure 18:
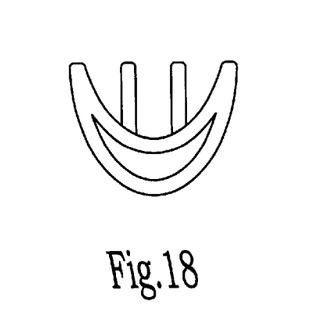
FIG. 18 is a cross-sectional view of a membrane component of the aneurysm shield of the present invention in a folded position.
Figure 19:
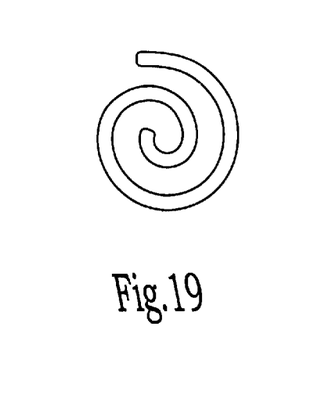
FIG. 19 is a cross-sectional view of an aneurysm shield membrane of the present invention in an alternate folded position.

An anchor ring such as shown at 60, 70 in FIGS. 9A, 9B and 10 is expandable by a device such as a balloon. This type of expansion is shown at 80 in FIG. 16. Anchor rings 70 are shown as being expanded by a balloon 82. With this embodiment, the aneurysm shield 84 is also expanded.

Because the anchor rings are of small size, the rings can traverse the tortuosity of cerebral anatomy while providing sufficient anchoring of the aneurysm shield main body to prevent any potential migration of material.

As shown in the various embodiments described herein, rings may be used in sequence. Furthermore, rings may be used with connections between them. The connections may be either metal or polymer. The rings may also be used independently of each other.

Figure 13:
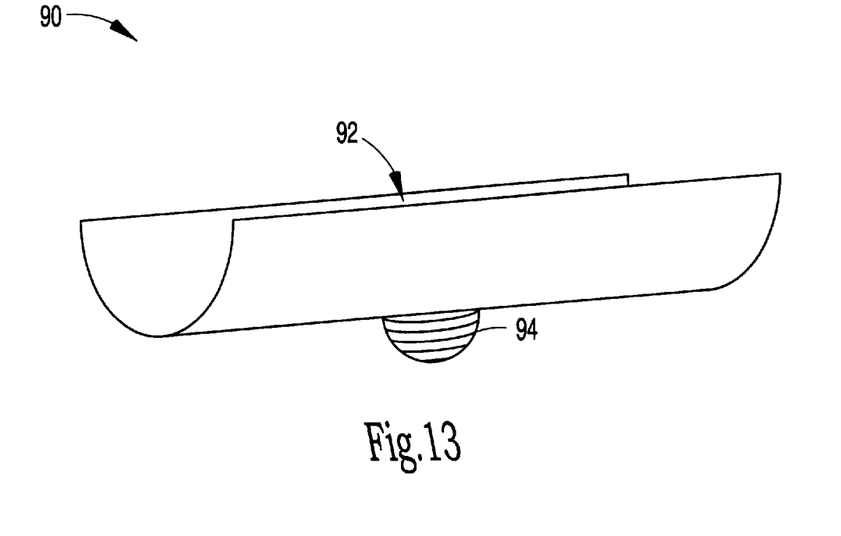
FIG. 13 is a perspective view of one embodiment of an aneurysm shield of the present invention that includes a swellable hydrogel bit.
Figure 14:
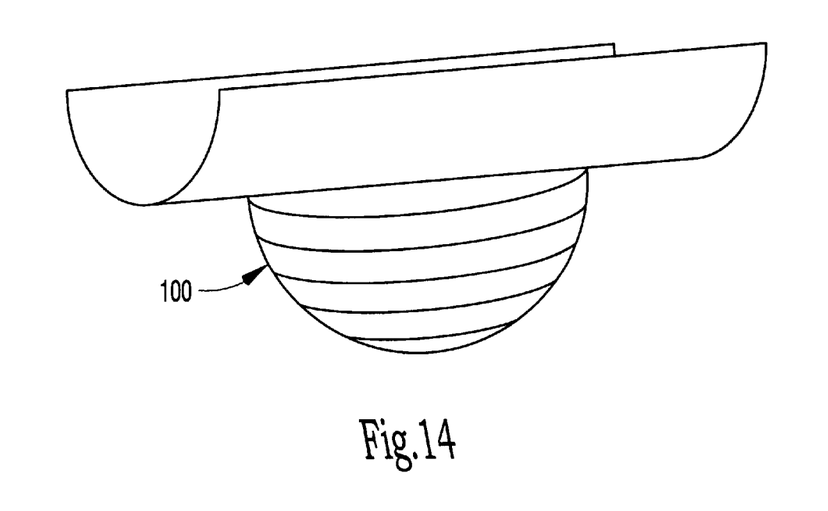
FIG. 14 is a perspective view of another aneurysm shield of the present invention with a neck plug.
Figure 15:
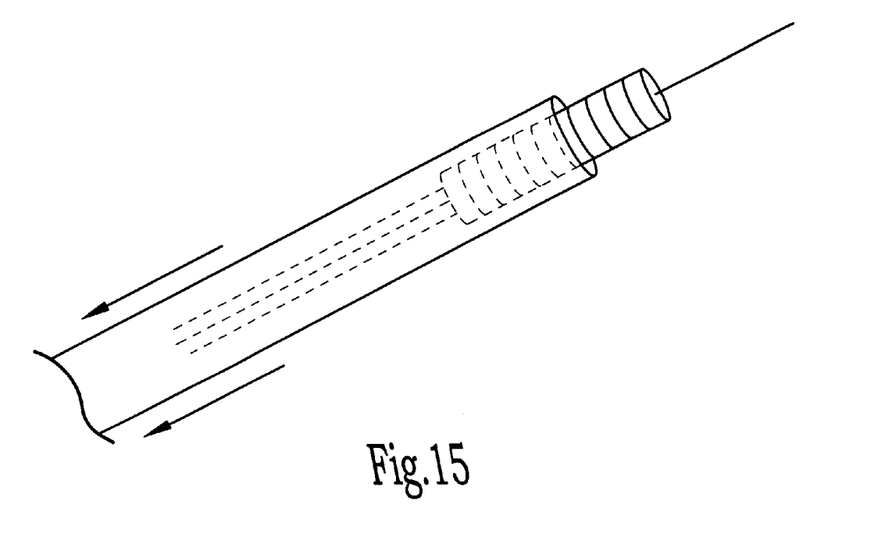
FIG. 15 is a cross-sectional view of one embodiment of the aneurysm shield of the present invention transported through a vessel over a guide wire.

One embodiment illustrated at 90 and FIG. 13 includes an aneurysm shield main body 92, with a swellable polymer bit 94, that is positioned on an inside surface, facing the aneurysm. The material, such as is shown in FIG. 14, swells, and the polymer or similar material fills the neck of the aneurysm beyond the shield, further sealing and supporting the shield. The use of the polymer positioned at the neck of an aneurysm acts as a secondary aneurysm closure. The polymer may have a swell ratio of 2:1 to 100:1 and swells by absorption of water over time to form a secondary foam plug and to add further closure and mechanical support at the neck of the aneurysm.

From the foregoing description, various modifications and changes in the composition and method will occur to those skilled in the art. All such modifications coming within the scope of the appended claims are intended to be included herein.

What is claimed is:

1. A device for covering an aneurysm, comprising:
   an elastic main body that has a half-cylindrical symmetry effective for covering an aneurysm; and
   one or more anchor rings for anchoring the main body about an aneurysm.

2. The device of claim 1 wherein the anchor rings are self-expanding.

3. The device of claim 1 wherein the anchor rings are balloon expanded.

4. The device of claim 1 wherein the main body comprises a surface facing the blood flow.

5. The device of claim 4 wherein the surface is coated with a material that promotes cellular growth.

6. The device of claim 1 wherein the main body comprises a surface that faces vessel wall.

7. The device of claim 6 wherein the surface is coated with a sticky material.

8. The device of claim 1 wherein the main body is comprised of a material selected from the group consisting of hydrogels, chitosan, alginate, and siloxane.

9. A method for treating an aneurysm, comprising:
   providing an elastic main body that has a half-cylindrical symmetry effective for covering the aneurysm and one or more anchor rings for anchoring the main body about the aneurysm;
   positioning the elastic main body over the aneurysm; and
   deploying the anchor rings at one or more locations of the main body.

10. The method of claim 9 wherein the anchor rings are self expanding.

11. The method of claim 9 wherein the anchor rings are expanded by a balloon.

12. The method of claim 9 wherein the main body is expanded by a balloon.

13. A method for repairing an aneurysm, comprising:

providing an elastic half-cylindrical main body that is positionable over an aneurysm;

imparting cell growth factors or genes or gene products to the main body effective to promote cell growth over the aneurysm; and anchoring the main body over the aneurysm with an anchoring mechanism.

14. The method of claim 13 wherein the anchoring mechanism comprises one or more anchor pins.

15. A device for treating an aneurysm, comprising:

an elastic main body that has a half cylindrical symmetry effective for covering the aneurysm;

an anchoring mechanism for anchoring the main body over the aneurysm; and a swellable material attached to the main body of a symmetry effective for substantially filling the neck of the aneurysm.

16. The device of claim 15 wherein the main body comprises cell growth factors or genes or gene products.

17. The device of claim 15 wherein the anchoring mechanism comprises anchor rings.

18. The device of claim 15 wherein the swellable material is a hydrogel.

\* \* \* \* \*